US00PP27539P3

(12) United States Plant Patent
Pavlich

(10) Patent No.: US PP27,539 P3
(45) Date of Patent: Jan. 10, 2017

(54) ***HEUCHERA* PLANT NAMED 'BLONDIE IN LIME'**

(50) Latin Name: ***Heuchera* sp.**
Varietal Denomination: Blondie in Lime

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 106 days.

(21) Appl. No.: 14/545,498

(22) Filed: May 12, 2015

(65) Prior Publication Data

US 2016/0338251 P1 Nov. 17, 2016

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu

(74) *Attorney, Agent, or Firm* — Klarquist Sparkman, LLP; Sheree Rybak

(57) ABSTRACT

A new and distinct *Heuchera* plant characterized by medium small lime green leaves, yellow green flowers in wands, being very free flowering, small, multi-crowned, low mounding habit, and excellent vigor.

1 Drawing Sheet

Botanical denomination: *Heuchera* sp.
Variety designation: 'Blondie in Lime'.

BACKGROUND OF THE INVENTION

The present invention relates to a new and distinct cultivar of *Heuchera* and given the cultivar name of 'Blondie in Lime'. *Heuchera* is in the family Saxifragaceae. *Heuchera* 'Blondie in Lime' originated from a whole plant mutation *Heuchera* 'Blondie', U.S. Plant Pat. No. 24,564, in the tissue culture lab in Canby, Oreg.

Compared to the parent plant, *Heuchera* 'Blondie', the new cultivar has lime green leaves rather than red brown and yellow green flowers rather than yellow green to creamy yellow.

Compared to *Heuchera* 'Lime Rickey', U.S. Plant Pat. No. 16,210, the new cultivar has smaller leaves that are unruffled, a smaller more compact habit, shorter wand type flowers that bloom all spring summer and fall rather than non-wand type that bloom in spring, and flowers that are yellow green rather than white.

This new *Heuchera* is uniquely distinguished by:

1. medium small lime green leaves,
2. yellow green flowers in wands,
3. being very free-flowering,
4. small, multi-crowned, low mounding habit, and
5. excellent vigor.

This new cultivar has been reproduced only by asexual propagation (tip cuttings and tissue culture). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 6 month-old plant of *Heuchera* 'Blondie in Lime' growing in a one gallon pot in a greenhouse in August in Canby, Oreg.

FIG. 2 shows an 8 month-old plant of *Heuchera* 'Blondie in Lime' growing in a one gallon pot in a cool greenhouse in September in Canby, Oreg.

DETAILED PLANT DESCRIPTION

The following is a detailed description of the new *Heuchera* cultivar based on observations of nine-month-old specimens growing in one gallon containers in a cool greenhouse in October in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 2007 edition.

Plant:

*Form.*—Basal rosette, herbaceous perennial.
*Hardiness.*—USDA Zone 4 to 9.
*Size.*—16 cm tall from top of the foliage to the ground and 42 cm wide.
*Habit.*—Mounding.
*Vigor.*—Excellent.
*Roots.*—Fibrous, freely branching, fine, and White 155A in color; roots develop easily from stem cuttings.

Leaf:

*Type.*—Simple.
*Arrangement.*—Rosette.
*Number.*—About 150.

*Shape*.—Broadly ovate to orbicular.
*Lobing/division*.—5 to 7 shallow lobes.
*Venation*.—Palmate.
*Margins*.—Broadly shallowly crenate.
*Apex*.—Mucronulate.
*Base*.—Cordate.
*Blade size*.—Grows to 10.5 cm long and 10 cm wide.
*Texture*.—Leathery.
*Surface texture*.—Glandular-puberulent on top and bottom.
*Petiole description*.—Grows to 15 cm long and 1.5 mm wide, glandular hairs, Yellow Green 146D.
*Leaf color*.—Early spring topside Yellow Orange 14B with veins 145C, bottom side Yellow 11B with veins 11C; top and bottom side, mid to late spring Yellow Green N144C with veins 145C, summer through winter Yellow Green 144A with veins 145C, bottom side 147C with veins 146D.

Inflorescence:
*Size*.—Grows to 4.5 cm wide and 9 cm long.
*Type*.—Upright thyrse.
*Number of flowers per thyrse*.—About 100.
*Number of thyrse*.—About 25 in the first spring flush, reblooming all summer.
*Peduncle*.—Grows to 20.5 cm long, 3 mm wide at base, Yellow Green 146C, glandular hairs.
*Pedicel*.—Variable in size, with glandular hairs, Yellow Green 146C.
*Bloom period*.—April through October in Canby, Oreg.

Flower bud:
*Size*.—2.5 mm wide and 3 mm long.
*Description*.—Glandular puberulent, ovoid, down facing.
*Color*.—Yellow Green N144D.

Flower:
*Type*.—Perfect.
*Shape*.—Campanulate.
*Attitude*.—Side to down-facing.
*Size*.—4.5 mm long and 3.5 mm wide.
*Corolla description*.—5 petals, 2 mm long and 0.5 mm wide, narrowly spatulate, margins entire, tip acute, glabrous top and bottom, White NN155C.
*Calyx description*.—Campanulate, 4.5 mm long and 3.5 mm wide, with 5 lobes divided ½ way to the base, each 1.6 mm wide and 1.6 mm long, glandular hairs outside and glabrous inside, tips obtuse, margin entire; color both sides Yellow Green 146D.
*Stamen description*.—5 in number, filaments 2 mm long, White NN155C, anthers 0.2 mm, Greyed Orange 177A, pollen none.
*Pistil description*.—1, 2-beaked, 4 mm long and 2 mm wide; Yellow Green 145C overall, ovary 1.5 mm long and 1.5 mm wide; style 2.5 mm long.
*Fragrance*.—None.
*Lastingness*.—Each thyrse blooms for about 3 weeks on the plant.

Fruit:
*Type*.—Two-beaked ovoid capsule.
*Size*.—4 mm long and 3 mm wide.
*Description*.—5 mm long and 5 mm wide, glandular puberulent, Greyed Brown 199C.
*Fertility*.—Low.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

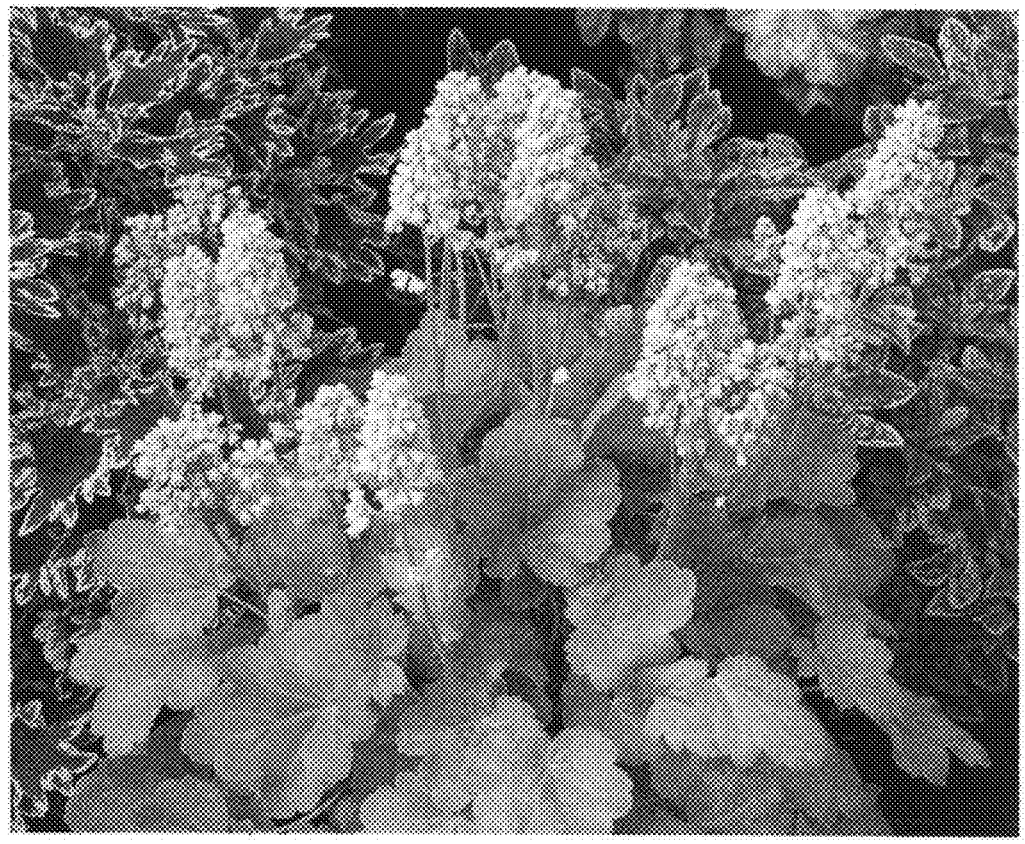

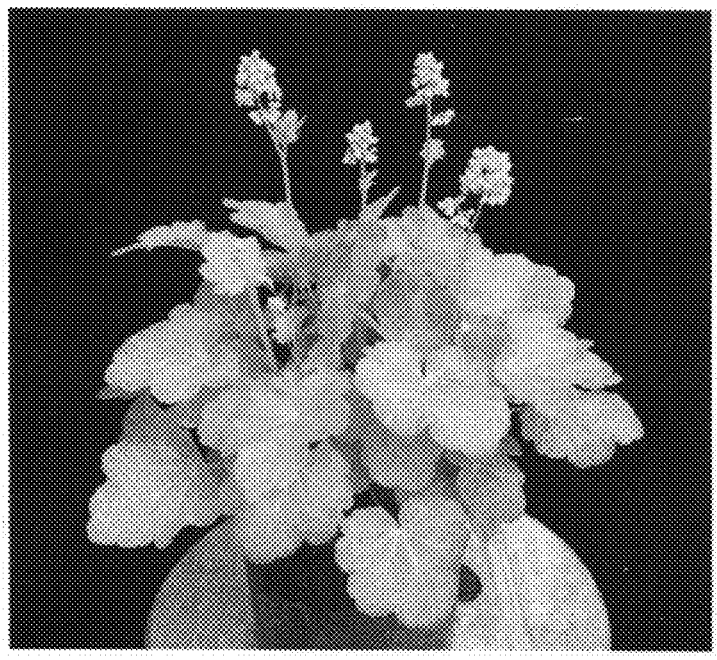
FIG. 1 left,
FIG. 2 below